US008515004B2

(12) United States Patent
Star-Lack et al.

(10) Patent No.: US 8,515,004 B2
(45) Date of Patent: Aug. 20, 2013

(54) REAL-TIME MOTION TRACKING USING TOMOSYNTHESIS

(75) Inventors: Josh Star-Lack, Palo Alto, CA (US); Hassan Mostafavi, Los Altos, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 351 days.

(21) Appl. No.: 12/912,786

(22) Filed: Oct. 27, 2010

(65) Prior Publication Data

US 2011/0058647 A1 Mar. 10, 2011

Related U.S. Application Data

(63) Continuation-in-part of application No. 12/354,800, filed on Jan. 16, 2009, now Pat. No. 7,831,013.

(51) Int. Cl.
*G01N 23/083* (2006.01)
*H05G 1/64* (2006.01)

(52) U.S. Cl.
USPC .............................. 378/23; 378/21; 378/98.12

(58) Field of Classification Search
USPC .................. 378/21–27, 92, 210, 901, 62, 91, 378/98.8, 98.12, 204
See application file for complete search history.

(56) References Cited

U.S. PATENT DOCUMENTS

| | | | |
|---|---|---|---|
| 3,809,886 A | 5/1974 | Cochran et al. | |
| 6,256,364 B1 | 7/2001 | Toth | |
| 6,823,044 B2* | 11/2004 | Rosner | 378/98.8 |
| 7,806,588 B2 | 10/2010 | Brunner et al. | |
| 2003/0043962 A1* | 3/2003 | Lai | 378/23 |
| 2003/0095631 A1* | 5/2003 | Rosner | 378/98.12 |
| 2004/0008809 A1* | 1/2004 | Webber | 378/8 |
| 2007/0025509 A1 | 2/2007 | Pang | |
| 2007/0237290 A1 | 10/2007 | Mostafavi | |
| 2007/0280407 A1* | 12/2007 | Kunze et al. | 378/4 |
| 2007/0291895 A1 | 12/2007 | Yin et al. | |
| 2009/0283682 A1 | 11/2009 | Star-Lack et al. | |
| 2010/0172561 A1 | 7/2010 | Ota et al. | |
| 2010/0172563 A1* | 7/2010 | Hagiwara | 382/131 |
| 2010/0183118 A1 | 7/2010 | Star-Lack et al. | |

OTHER PUBLICATIONS

PCT Notification of Transmittal of the International Search Report and the Written Opinion of the International Searching Authority, or the Declaration, Apr. 2, 2010.
Supplementary European Search Report, Apr. 30, 2012.
Jonathan S. Maltz et al., "Fixed Gantry Tomosynthesis System for Radiation Therapy Image Guidance Based on a Multiple Source X-Ray Tube with Carbon Nanotube Cathodes", Medical Physics, AIP, Melville, NY, US, Apr. 13, 2009, pp. 1624-1636, vol. 36, No. 5.

(Continued)

*Primary Examiner* — Anastasia Midkiff
(74) *Attorney, Agent, or Firm* — SU IP Consulting

(57) ABSTRACT

One embodiment of the present disclosure sets forth a method for determining a movement of a target region using tomosynthesis. The method includes the steps of accessing a first set of projection radiographs of the target region over a first processing window defined by a first range of projection angles, accessing a second set of projection radiographs of the target region over a second processing window defined by a second range of projection angles, wherein the first processing window moves to the second processing window, and comparing a first positional information derived from the first set of the projection radiographs and a second positional information derived from the second set of the projection radiographs with the first positional information to determine the movement of the target region.

19 Claims, 12 Drawing Sheets

(56) References Cited

OTHER PUBLICATIONS

Notification of Transmittal of the International Search Report and the Written Opinion of the International Searching Authority, Dec. 23, 2011.

Gupta et al., "Flat-Panel Volume CT: Fundamental Principles, Technology, and Applications," Radiographics: The Journal of Continuing Medical Education in Radiology, 2009 [Retrieved from internet: <URL: http://radiographics.rsna.org/content/28/7/2009.full>].

* cited by examiner

REAL-TIME MOTION TRACKING USING TOMOSYNTHESIS

CROSS-REFERENCE TO RELATED APPLICATIONS

This application is a continuation-in-part of U.S. patent application Ser. No. 12/354,800, filed Jan. 16, 2009.

BACKGROUND

Unless otherwise indicated herein, the approaches described in this section are not prior art to the claims in this application and are not admitted to be prior art by inclusion in this section.

Various systems and methods exist to provide radiation therapy treatment of tumorous tissue with high-energy radiation. Many forms of radiation treatment benefit from the ability to accurately control the amount, location, and distribution of radiation within a patient's body. Such control often includes using a multi-leaf collimator to shape a radiation beam to approximate that of the tumorous region.

Many existing radiation treatment procedures require a location of a target region to be determined in order to accurately register the target region relative to a radiation source before radiation is applied to the target region. Computed tomography ("CT") is an imaging technique that has been widely used in the medical field. In a procedure for CT, an x-ray source and a detector apparatus are positioned on opposite sides of a portion of a patient under examination. The x-ray source generates and directs an x-ray beam towards the patient, while the detector apparatus measures the x-ray absorption at a plurality of transmission paths defined by the x-ray beam during the process. The detector apparatus produces a voltage proportional to the intensity of incident x-rays, and the voltage is read and digitized for subsequent processing in a computer. By taking a plurality of readings from multiple angles around the patient, relatively massive amounts of data are thus accumulated. The accumulated data are then analyzed and processed for reconstruction of a matrix (visual or otherwise), which constitutes a depiction of a density function of a volume of the bodily region being examined. Cone-bream computed tomography imaging (CBCT) which uses a flat panel detector is typically used in radiation therapy systems.

CT has found its principal application in examination of bodily structures or the like which are in a relatively stationary condition. In some cases, it may be desirable to continuously monitor a position of a target region while a treatment procedure is being performed. However, currently available apparatus that supports CT may not be able to generate tomographic images with sufficient quality or accuracy in part due to intra-fraction motion caused by inadvertent patient shifts or natural physiological processes. For example, breathing or expelling gas through the rectum has each been shown to cause degradation of quality in CT images. In such cases, it would be desirable to track a movement of the target region to ensure that a treatment radiation beam is accurately aimed towards the target region. In existing radiation treatment systems, tracking of the target region does not use a CT imaging technique. This is because collecting a sufficient quantity of CT image data for image reconstruction may take a long time, and therefore may not be performed at a fast enough rate to provide sufficiently current information to adjust the treatment radiation beam.

Another approach to 3D localization is "3D point tracking" which relies on taking individual projection radiographs and localizing high density implanted fiducial markers in each projection, for example by using the pixel coordinates of the markers' centroids. Then triangulation is performed to find the 3D position of a marker by using different radiographs taken at different projection angles. However, finding the pixel coordinates of a high density marker in a single X-ray projection can be difficult. Overlaying anatomy and external structures are an important source of failure of these techniques. Very often, the X-ray quantum noise and scattered radiation result in the failure to detect or localize a marker using automatic image analysis algorithms.

Conventional portal imaging techniques use treatment "beam's-eye view" ("BEV") imaging to track both inter- and intra-fraction motion. One drawback is that most BEV imaging occurs at MV energies, which is less dose-efficient than imaging at kilo-volt (kV) energies. Another drawback is that, if high density fiducial markers are used, the markers may not be exposed to BEV at all times, thus causing treatment to be interrupted for purposes of repositioning the multi-leaf collimator blades. Interruption of treatment is particularly undesirable for arc-therapies.

Some radiation therapy treatment systems are equipped with kV imaging systems mounted to the gantry whose projection angle is orthogonal to the treatment beam. The imaging techniques used with such an orthogonal system also can include CT imaging and 3D point tracking. An advantage of the kV system is its higher dose efficiency. Moreover, the imaging target can be exposed at all times during treatment since the kV source is only used for imaging. Nevertheless, the motion-related problems with full CT acquisitions still exist as can SNR and other limitations associated with acquiring a single projection radiograph for 3D point tracking.

BRIEF DESCRIPTION OF THE DRAWINGS

So that the manner in which the above recited features of the disclosure can be understood in detail, a more particular description of the disclosure may be had by reference to embodiments, some of which are illustrated in the drawings. It is to be noted, however, that the drawings illustrate only typical embodiments and are therefore not to be considered limiting of its scope, for the disclosure may admit to other equally effective embodiments.

DETAILED DESCRIPTION

Various embodiments are described hereinafter with reference to the figures. It should be noted that the figures are not drawn to scale. It should also be noted that the figures are only intended to facilitate the description of embodiments. They are not intended as an exhaustive description of the disclosure or as a limitation on the scope of the disclosure. In addition, an aspect described in conjunction with a particular embodiment is not necessarily limited to that embodiment and can be practiced in any other embodiments.

Figure 1:
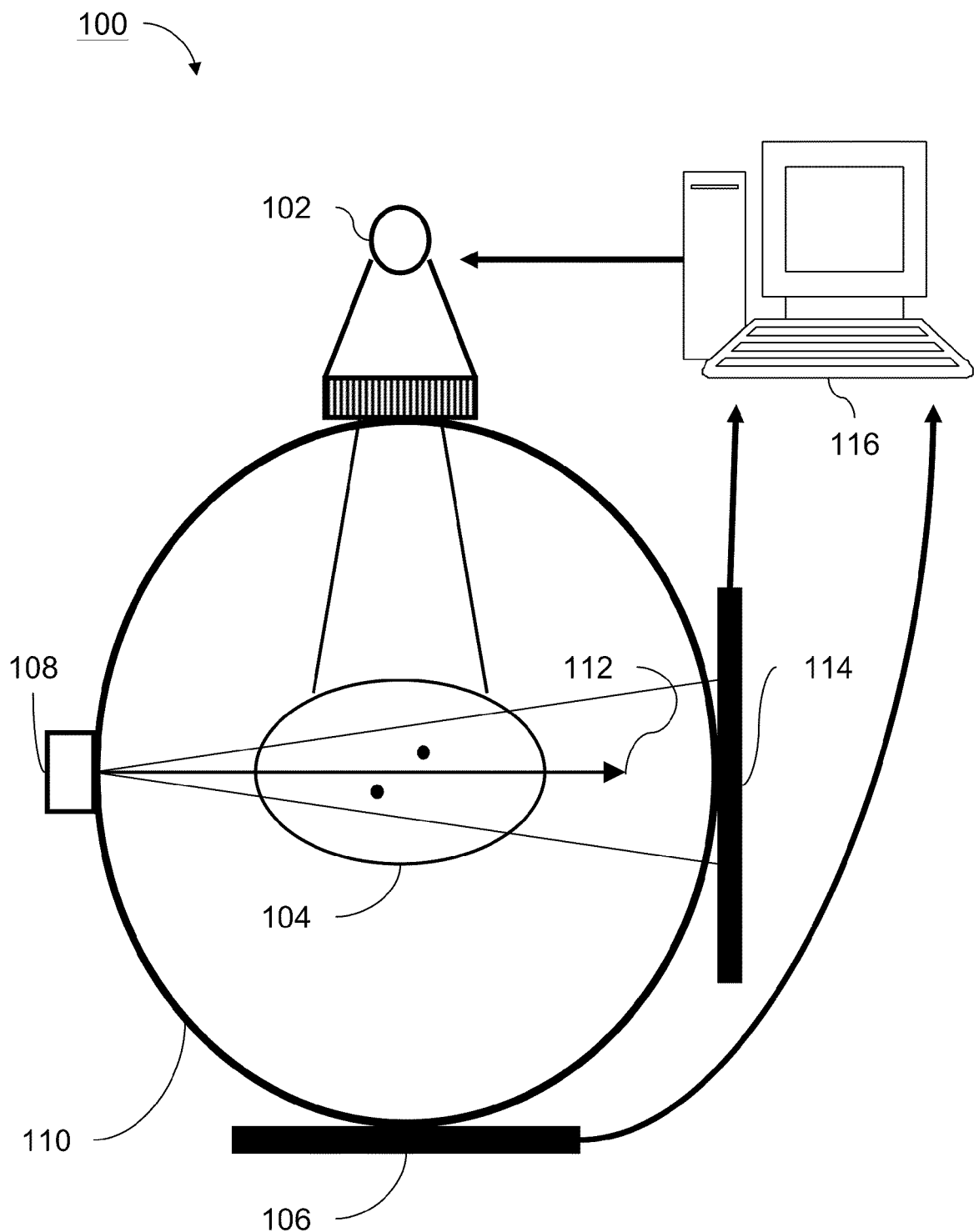
FIG. 1 is a schematic diagram illustrating a treatment radiation system, according to one embodiment of the disclosure.

FIG. 1 is a schematic diagram illustrating a treatment radiation system 100, according to one embodiment of the disclosure. The treatment radiation system 100 includes a first radiation source 102, an electronic portal imaging device (EPID) 106, a second radiation source 108 mounted on a gantry 110, a flat panel detector 114, and a control system 116. The first radiation source 102 is aimed towards a patient 104 and to the EPID 106. The patient 104 has markers, which may be high density objects that can be localized using x-ray projection radiographs. Some examples of a marker include, without limitation, a bone, a surgical clip, or other high contrast object. In one scenario, the patient 104 may have a prostate gland implanted with gold marker beads.

In one implementation, the second radiation source 108 is situated at a right angle to the first radiation source 102. A radial direction (r) 112 here is defined as the direction from the second radiation source 108 through the isocenter to the flat panel detector 114. The information acquired by the treatment radiation system 100 is analyzed by the control system 116, which adjusts the first radiation source 102 and the rotation of the gantry 110 accordingly.

In the illustrated embodiments, the first radiation source 102 is a treatment radiation source for providing treatment energy with a collimator system for controlling a delivery of the treatment beam, and the second radiation source 108 is an imaging radiation source. In other embodiments, in addition to being a treatment radiation source, the first radiation source 102 can also provide imaging data. In other embodiments, the first radiation source 102 can provide imaging data without providing treatment energy. The treatment energy generally refers to those energies of 160 kilo-electron-volts(keV) or greater, and more typically 1 mega-electron-volts (MeV) or greater. The imaging energy can include treatment energies and also energies below the high energy range, more typically below 160 keV.

In the illustrated embodiments, the control system 116 includes a processor for executing instructions, a monitor for displaying data, and an input device, such as a keyboard or a mouse, for inputting data. In the illustrated embodiments, the gantry 110 is rotatable, and during a treatment session, the gantry 110 rotates about the patient 104, as in an arc-therapy. Here, "treatment session" generally refers to the session in which the patient 104 is imaged and/or treated. The operations of the first radiation source 102, the collimator system, and the gantry 110 are controlled by the control system 116, which provides power, timing, rotation, and position control based on received signals. Although the control system 116 is shown as a separate component from the gantry 110, in alternative embodiments, the control system 116 can be a part of the gantry 110.

It should be noted that the treatment radiation system 100 should not be limited to the configuration described above, and that the system can also have other configurations. For example, instead of the shown ring-configuration, the system can include a C-arm or other types of an arm to which the first radiation source 102 or the second radiation source 108 is secured. It should also be noted that the treatment radiation system 100 can have one or more radiation sources. Other configurations may include a single radiation source with multiple detectors, or multiple sources with a single detector.

Figure 2:
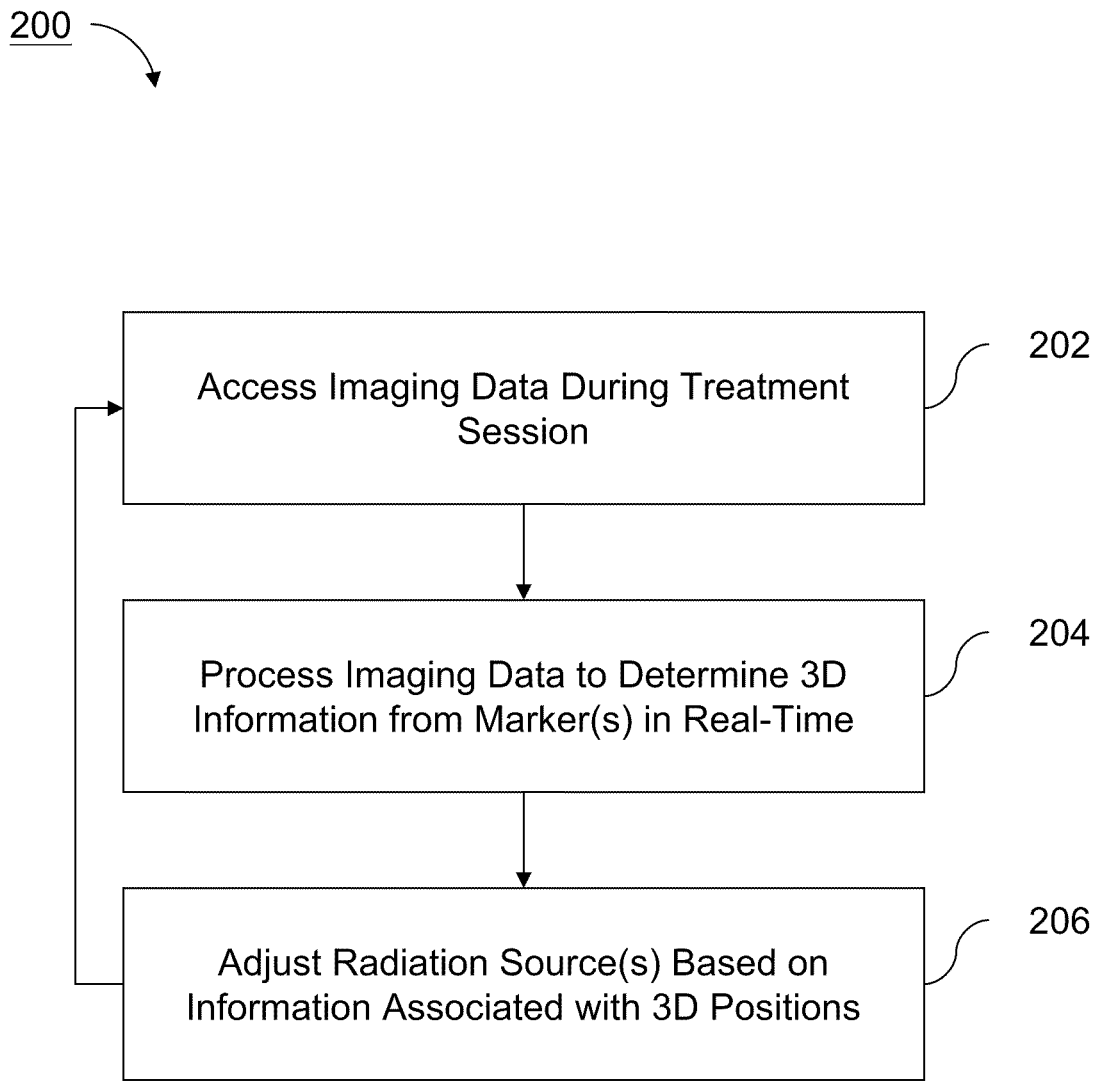
FIG. 2 is a flow chart illustrating a method of performing real-time tracking using tomosynthesis, according to one embodiment of the disclosure.

FIG. 2 is a flow chart illustrating a method 200 of performing real-time motion tracking using tomosynthesis, according to one embodiment of the disclosure. In conjunction with FIG. 1, in step 202, the control system 116 accesses imaging data during a treatment session. Here, "imaging data" generally refers to projection radiographs, which as discussed above, can come from the first radiation source 102, the second radiation source 108, or a combination of the two sources. In step 204, the control system 116 processes the imaging data to determine 3D information from the markers during the treatment session. In step 206, the control system 116 adjusts the radiation source(s) based on information associated with 3D positions. Here, "real-time motion tracking" broadly refers to the motion tracking that occurs while the treatment session is ongoing. Similarly, "real-time adjustment" of the first radiation source 102 also broadly refers to the adjustment that occurs while the treatment session is ongoing. Steps 202, 204, and 206 are performed concurrently with treatment and repeated until the session ends. Each of the above steps is performed independently from the other steps. They may also be performed simultaneously.

Before the treatment session begins in step 202, the patient 104 of FIG. 1 is set-up and positioned on the treatment radiation system 100. Set-up may involve acquiring projection radiographs to localize the markers for comparison with digitally reconstructed radiographs from a reference scan. Alternatively, Cone Beam CT (CBCT) may be used to localize both soft tissue and markers. The position of the patient 104 is adjusted according to the localization information.

Independent from step 202, in one implementation, the gantry rotates continuously, and the second radiation source 108 and the flat panel detector 114 are used to acquire projection radiographs at regularly spaced intervals. In another implementation, the second radiation source 108 and the flat panel detector 114 are used to acquire imaging data with gaps in a certain angular range. In yet another implementation, the second radiation source 108 and the flat panel detector 114 are used to acquire imaging data at predetermined gantry angles. In still another implementation, the control system 116 determines when the second radiation source 108 and the flat panel detector pair 114 are used to acquire imaging data based on optimization considerations. In one implementation, the second radiation source 108 and the flat panel detector 114 refer to the On-Board Imaging (OBI) system from Varian Medical Systems, Inc.

Alternatively, the first radiation source 102 and the EPID 106 can together also generate imaging data. For example, projection radiographs, acquired by the EPID 106 while using the first radiation source 102 at high energies (e.g., for treatment), may be used. In another example, projection radiographs, acquired by the EPID 106 while using the first radiation source 102 at low energies (e.g., for imaging), may be used.

In one implementation, during a treatment session, the first radiation source 102 is configured to alternate between delivering beams for treating a target region and delivering beams for generating imaging data for tomosynthesis. In another implementation, a combination of imaging data from utilizing the first radiation source 102 and the second radiation source 108 can be used for tomosynthesis. In implementations with multiple radiation sources, a combination of imaging data from the radiation sources can be used for tomosynthesis.

The radiation source adjustment in step 206 can be done in a number of ways. For example, the collimator blades of the first radiation source 102, the second radiation source 108, or the combination of the two radiation sources of FIG. 1 can be modulated so that the markers are irradiated to minimize the extra dose delivered to the patient 104. In addition, the position of the collimator blades may be adjusted during treatment whenever the markers are determined not to be in the field-of-view to maintain illumination of the markers. In another example, the dose may vary according to the projection angle. To illustrate, the dose for lateral views of the pelvis may be higher than the does for anterior-posterior views. This can be achieved either by adjusting the mAs per projection or by adjusting the projection density or sampling rate as a function of the projection angle.

Figure 3A:
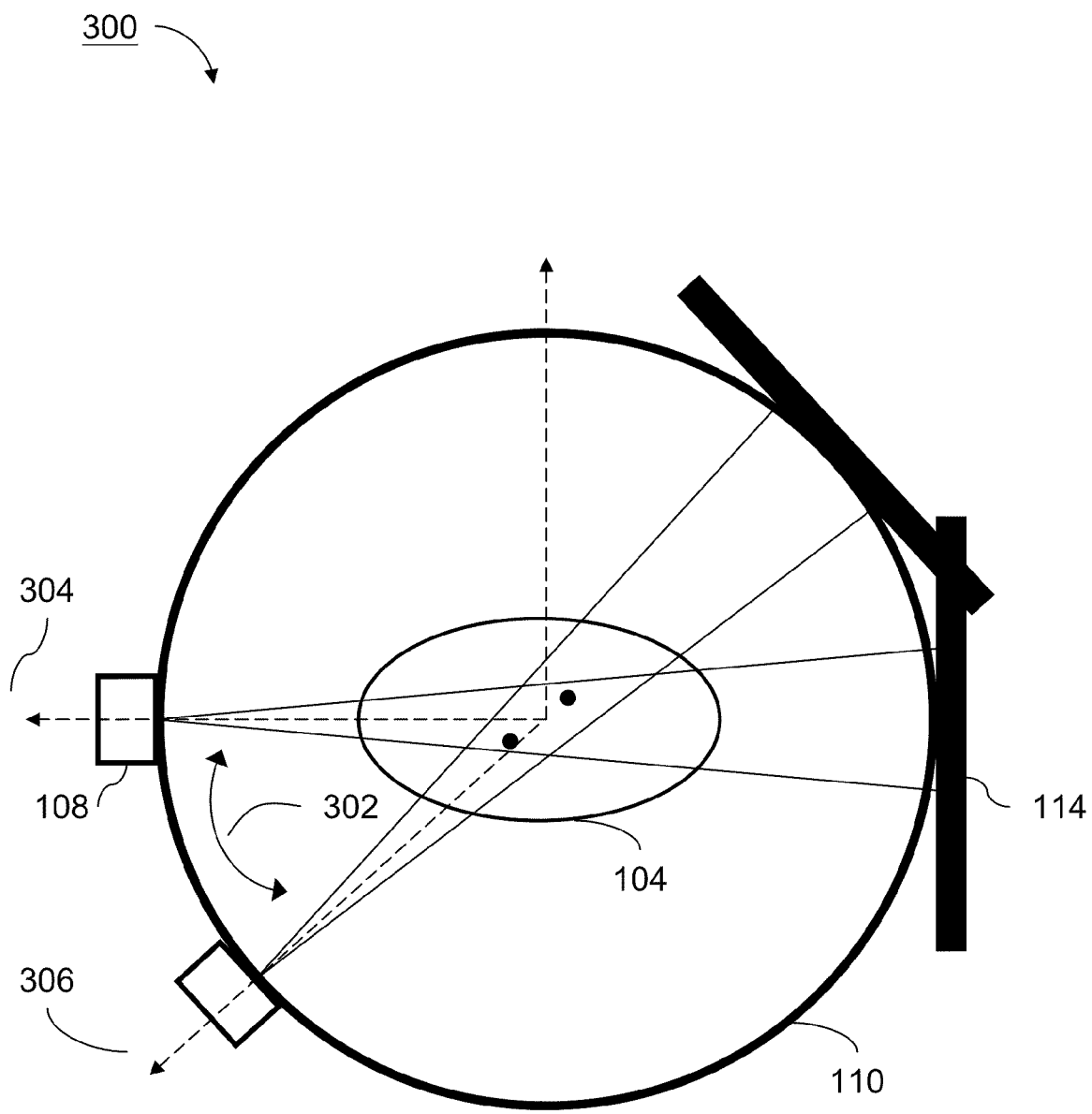
FIG. 3A is a schematic diagram illustrating a limited angle acquisition approach, according to one embodiment of the disclosure.

FIG. 3A is a schematic diagram 300 illustrating a limited angle acquisition approach, according to one embodiment of the disclosure. In conjunction with FIG. 1, here, the second radiation source 108 is aimed towards the patient 104 through to the flat panel detector 114. There are N projection radiographs in the sequence spanning an angular range $\Delta\theta$ 302 (also referred to as a "tomographic angle $\Delta\theta$ 302".) A first projection angle 304 is denoted as $\theta_{i-N+1}$. A last angle 306 is denoted as $\theta_i$, corresponding to current time point $t_i$, which is the most current time that imaging data is being acquired. In other implementations, the limited angle acquisition approach can be used by the first radiation source 102 or other radiation sources.

As mentioned above, in one implementation, the second radiation source 108 and the flat panel detector 114 pair can rotate 360° around the gantry 110 and about the patient 104 in an arcuate manner (e.g., in a counter clockwise or clockwise direction) and can generate an image every 1°. The second radiation source 108 and the flat panel detector 114 pair may also move in tandem. In other implementations, the second radiation source 108 and the flat panel detector 114 pair can be configured to rotate through a set of different rotational angles, generate a different number of images, or have gaps in the angular range over which the images are acquired.

Figure 3B:
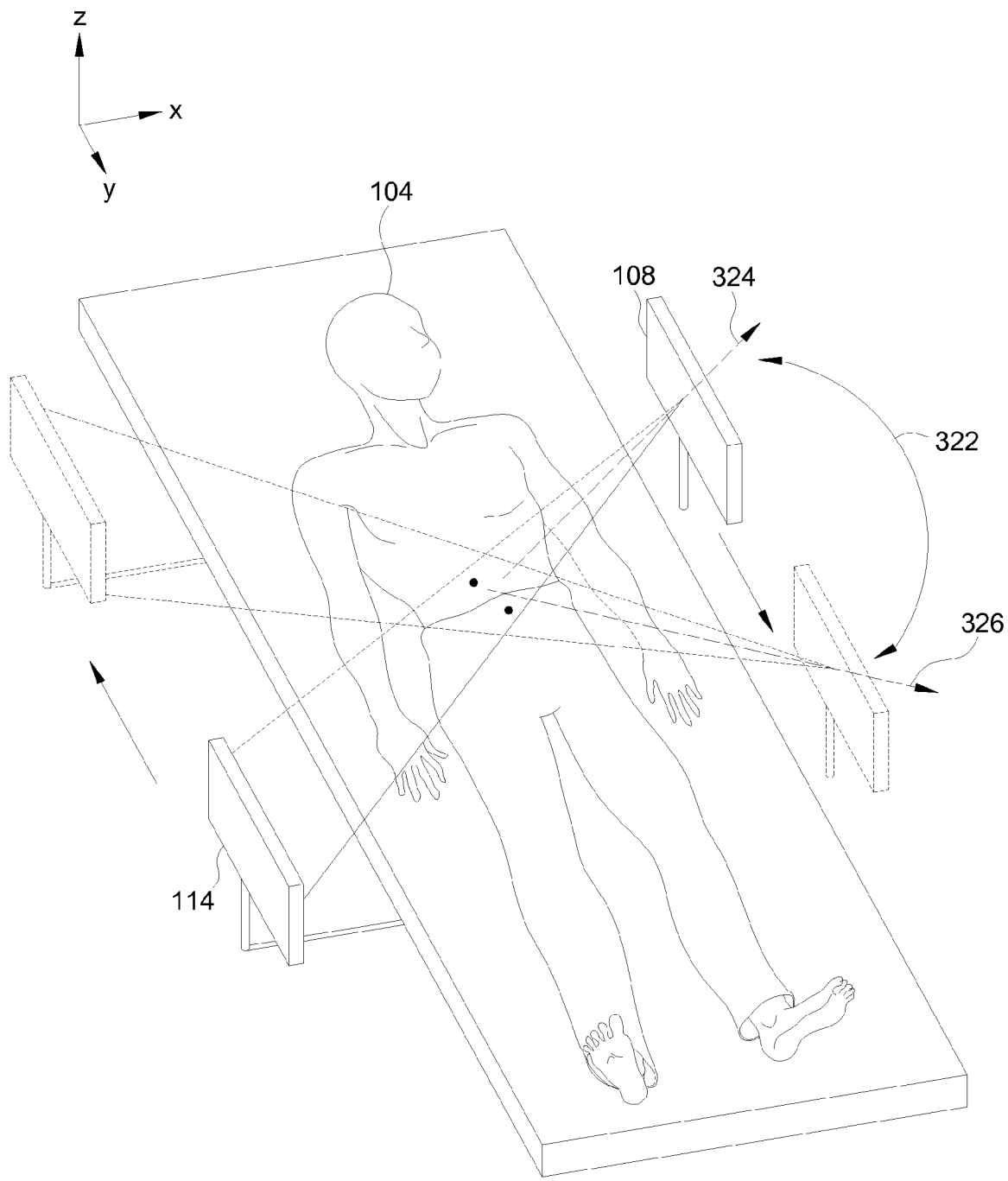
FIG. 3B is a schematic diagram illustrating another limited angle acquisition approach, according to one embodiment of the disclosure.

FIG. 3B is a schematic diagram 320 illustrating another limited angle acquisition approach, according to one embodiment of the disclosure. In conjunction with FIG. 1, the second radiation source 108 is aimed towards the patient 104 through to the flat panel detector 114. There are N projection radiographs in the sequence spanning an angular range $\Delta\theta$ 322 (also referred to as a "tomographic angle $\Delta\theta$ 322".) A first projection angle 324 is denoted as $\theta_{i-N+1}$. A last angle 326 is denoted as $\theta_i$, corresponding to current time point $t_i$, which is the most current time that imaging data is being acquired.

In one implementation, unlike the configuration shown in FIG. 3A, the second radiation source 108 and the flat panel detector 114 may move in different directions. For example, suppose the patient 104 lays on a patient patent in an X-Y plane. The second radiation source 108 may move in a positive Y direction, while the flat panel detector 114 may move in a negative Y direction. In addition, rather than rotating 360° around the gantry 110 and the patient 104, the second radiation source 108 and the flat panel detector 108 pair may generate an image every 1° or another rotational angle from a side of the patient 104.

Figure 3C:
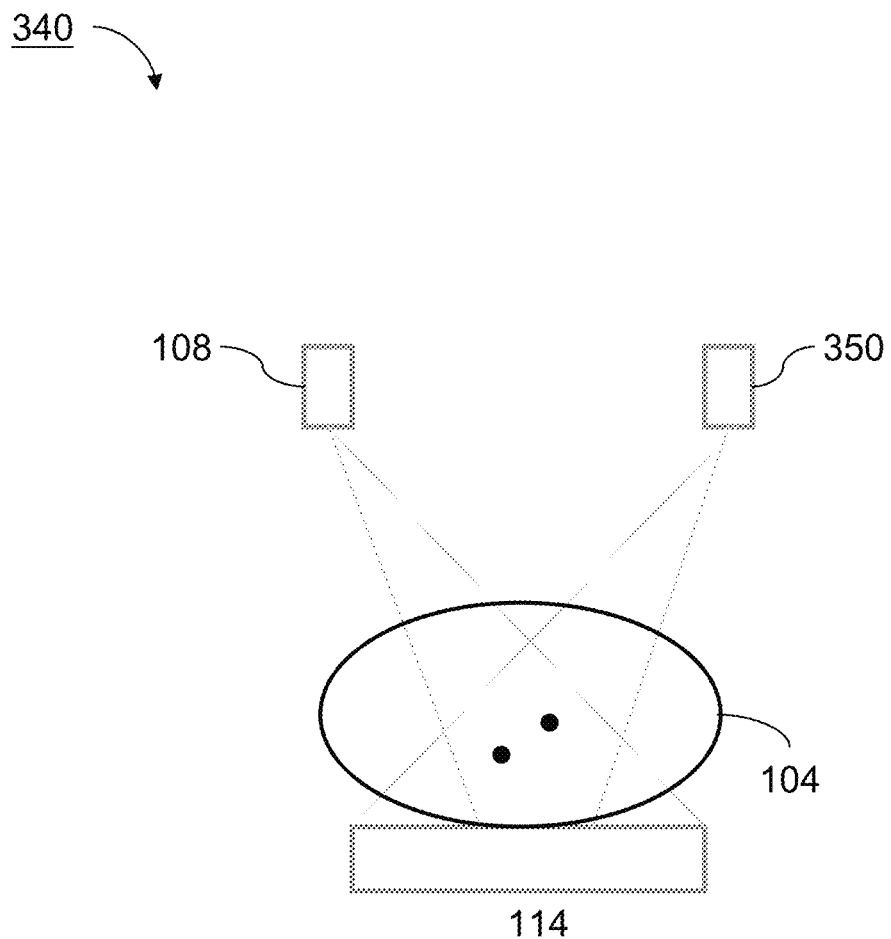
FIG. 3C is a side view schematic diagram illustrating yet another limited angle acquisition approach, according to one embodiment of the disclosure.

FIG. 3C is a side view of a schematic diagram 340 illustrating yet another limited angle acquisition approach, according to one embodiment of the disclosure. In conjunction with FIG. 1, the second radiation source 108 and optionally a third radiation source 350 are aimed towards the patient 104 through to the flat panel detector 114.

Figure 3D:
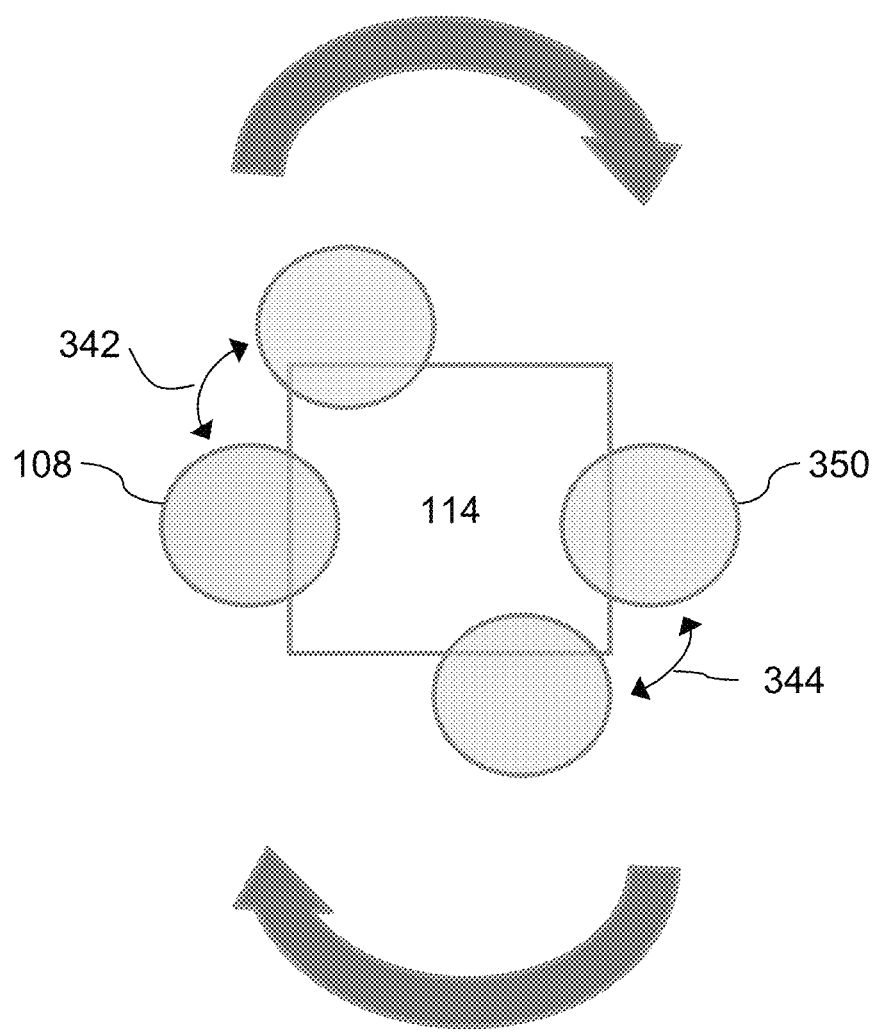
FIG. 3D is a top view schematic diagram illustrating the limited angle acquisition approach of FIG. 3C, according to one embodiment of the disclosure.

FIG. 3D is a top view of the same limited angle acquisition approach shown in FIG. 3C, according to one embodiment of the disclosure. The second radiation source 108 and the optional third radiation source 350 may rotate in a circle and in a first plane above the patient 104 and the flat panel detector 114. The flat panel detector 114 is in a second plane, which is in parallel to the first plane. There are M projection radiographs in the sequence spanning an angular range $\Delta\theta$ 342 (also referred to as a "tomographic angle $\Delta\theta$ 342") as the second radiation source 108 rotates clockwise. Similarly, there are also N projection radiographs in the sequence spanning an angular range $\Delta\theta$ 344 (also referred to as a "tomographic angle $\Delta\theta$ 344") as the third radiation source 350 rotates clockwise. In one implementation, M may not equal to N. Also, the rotation of the one or more radiation sources may occur independently from the rotation of a gantry, such as the gantry 110.

Figure 3E:
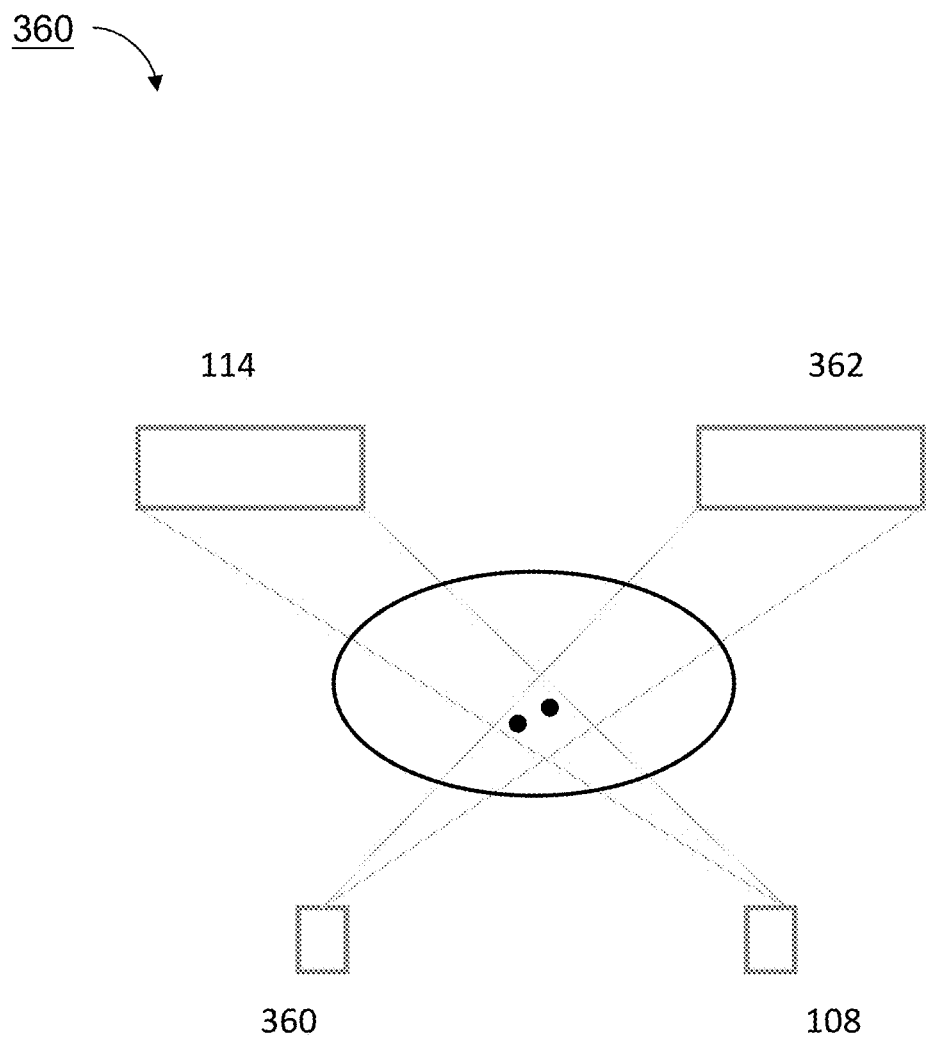
FIG. 3E is a side view schematic diagram illustrating another limited angle acquisition approach, according to one embodiment of the disclosure.

FIG. 3E is a side view of a schematic diagram 360 illustrating another limited angle acquisition approach, according to one embodiment of the disclosure. In conjunction with FIG. 1, the second radiation source 108 and optionally a third radiation source 360 are aimed towards the patient 104 through to the flat panel detector 114 and optionally a second flat panel detector 362. Unlike the approach shown in FIG. 3C (i.e., the flat panel detector 114 does not rotate), the second radiation source 108 and the third radiation source 360 may rotate in a circle and in a first plane, and the flat panel detector 114 and the second flat panel detector 362 may also rotate in a circle and in a second plane. The first plane is in parallel to the second plane. As a result, additional projection radiographs from different angular ranges may be acquired.

Figure 4:
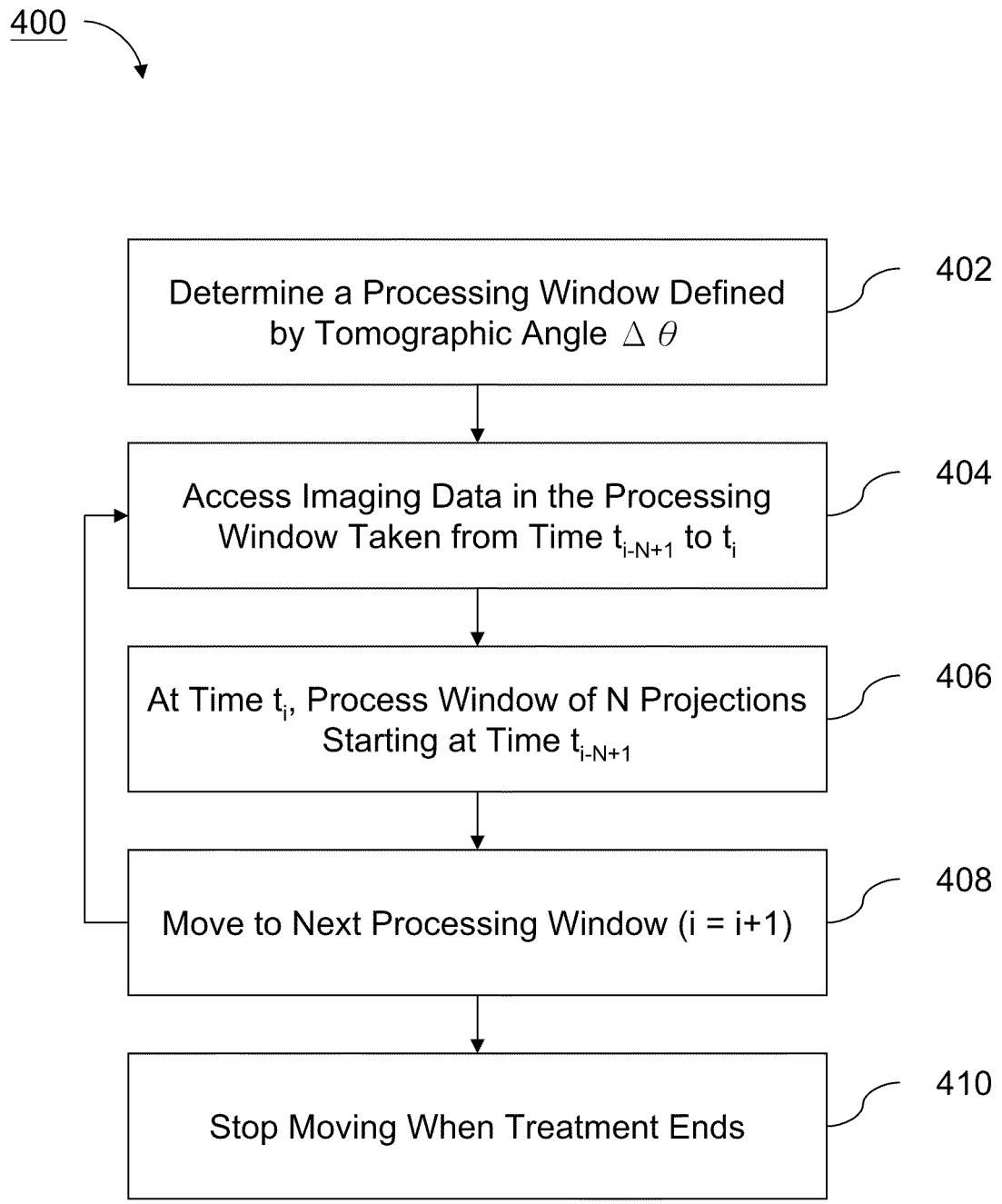
FIG. 4 is a flow chart illustrating a method of acquiring projection radiographs, according to one embodiment of the disclosure.

FIG. 4 is a flow chart illustrating a method 400 of acquiring projection radiographs, according to one embodiment of the disclosure. Using the approach shown in FIG. 3A as an example, in step 402, a processing window is defined by the tomographic angle $\Delta\theta$ 302. In one implementation, the processing window can range from 3° to 40°. The method 400 can be carried out by the first radiation source 102, the second radiation source 108, or other radiation sources in other implementations.

In conjunction with FIG. 1, in step 404, the control system 116 accesses the imaging data within the processing window taken from time $t_{i-N+1}$ to $t_i$, corresponding to the N projection radiographs taken between projection angles $\theta_{i-N+1}$ 304 to $\theta_i$ 306 in FIG. 3A. As an example, for a sliding arc window, the control system 116 accesses 21 projection radiographs taken between projection angles 20° and 40° (1 projection radiograph taken at each degree interval). In step 406, at time $t_i$, a window of N projection radiographs starting at time $t_{i-N+1}$, is processed. Two methods of processing the windows of projection radiographs, sliding arc tomosynthesis and short arc tomosynthesis, are further described in conjunction with FIGS. 5A and 5B below.

Continuing with FIG. 4, in step 408, the control system 116 moves on to the next processing window (i=i+1). The moving of the processing window 302 may occur while treatment is still ongoing so that at the next time increment $t_{i+1}$ the projection radiograph at time $t_{i-N+1}$ may be dropped. If the coordinates of the backprojection matrix do not rotate in place with the acquisition, then processing may continue by subtracting the projection radiograph at $t_{i-N+1}$ and adding the projection radiograph at time $t_{i+1}$. In the above sliding arc example, at the next time increment, the projection radiograph at the projection angle 20° is dropped, and the new projection radiograph taken at this time increment, corresponding to projection angle 41°, is added. In other words, the processing window 302 slides to encompass projection angles 21° through 41°. Steps 404, 406, and 408 are repeated throughout the treatment period. In the example above, 21 projection radiographs from 21° to 41° are first processed. Then 21 projection radiographs from 22° to 42° are subsequently processed, and so on, with the 20° processing window sliding over 1° at each time increment. In an optional step 410, the movement of the processing windows ends when treatment ends.

Figure 5A:
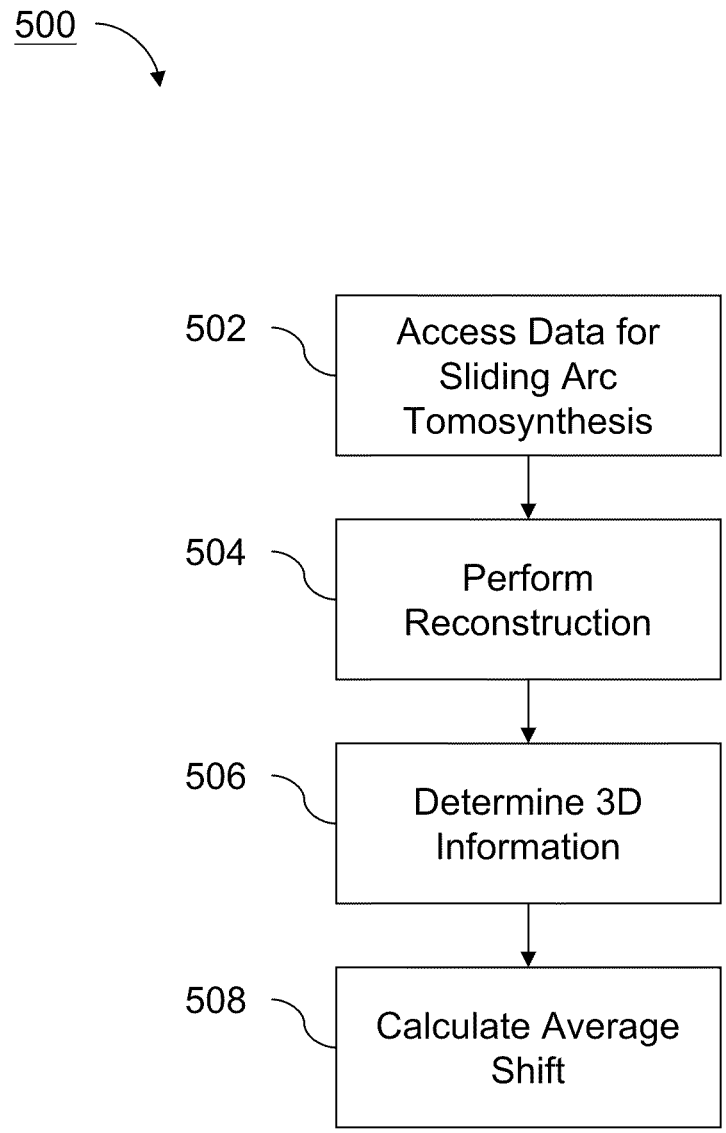
FIG. 5A is a flow chart illustrating a method of processing projection radiographs using sliding arc tomosynthesis, according to one embodiment of the disclosure.

FIG. 5A is a flow chart illustrating a method 500 of processing projection radiographs using sliding arc tomosynthesis, according to one embodiment of the disclosure. The method 500 can be carried out by the first radiation source 102, the second radiation source 108, or other radiation sources in other implementations. Step 502 corresponds to step 202 of FIG. 2 and step 404 of FIG. 4. In conjunction with FIG. 1 and the example above for sliding arc tomosynthesis, the control system 116 accesses 21 projection radiographs for each 20° processing window. Steps 504, 506, and 508 further illustrate steps 204 and 406. At time $t_i$, a window of N projection radiographs starting at time $t_{i-N+1}$, is processed. In step 504, reconstruction using techniques such as, without limitation, backprojection or filtering. Step 504 can also include preprocessing techniques, such as, without limitation, performing logarithmic transforms. When more than one radiation source and/or more than one flat panel detector are utilized to acquire the radiograph projections (e.g., the approaches illustrated in FIGS. 3C, 3D, and 3E and discussed above), in one implementation, the different radiograph projections generated from distinct radiation source and flat panel detector pairs are processed using, for example, filtering and backprojection operations, to reconstruct an image. Other reconstruction methods may involve iterative techniques.

Backprojection is a common algorithm used in the tomographic reconstruction of clinical data. When an n-dimensional object is projected, each projection radiograph is an n−1 dimensional sum of its density along the projection axis. The reverse function is called back projection and regenerates the original object. In some implementations, the orientation of the backprojection matrix may rotate with the image acquisition system, which is a more "natural" coordinate system for tomosynthesis reconstruction. Here, the radial direction is defined as being parallel to the central projection angle $\theta_p = (\theta_{i-N+1} + \theta_i)/2$ of the imaging system and a lateral direction as being orthogonal to the radial direction. For tomosynthesis reconstruction, two axes of the backprojection (or reconstruction) matrix are in lateral directions while the third axis is directed in the radial direction which in general, has lower spatial resolution than the lateral axes. In alternative implementations, the backprojection matrix can be fixed in the normal Cartesian coordinate system (e.g., left-right, anterior-posterior, superior-inferior) used for imaging and radiotherapy. One common method of backprojection is known and "shift and add tomosynthesis." In particular, the projection radiographs acquired using the approach described in conjunction with FIG. 4 above are shifted and added in the plane of interest to bring the markers in focus, while structures in other planes are distributed and thus appear blurred.

Before backprojection is performed, the data may be processed to enhance certain spatial frequencies and depress others. An example is the frequency-domain ramp filter that is used for the Feldkamp, Davis, and Kress (FDK) reconstruction algorithm. Compensation may be made for $1/r^2$ effects as prescribed by the FDK algorithm. After backprojection, the data may be filtered to deblur the image. Deblurring techniques can include spatial frequency filtering selective plan removal, iterative restoration, matrix inversion, or other techniques known in the art.

In some implementations, fully iterative reconstruction methods are used where the data are first backprojected and then forward projected for comparison with the original projection radiographs. Examples of iterative techniques include, but are not limited to, ART, EM MLEM, and OSEM.

In step 506, the positions of the markers are determined. In one implementation, a different method is employed to identify the axis along the radial direction for the markers than the axes along the lateral directions. Some techniques for detecting the markers include, without limitation, calculating the 3D center-of-mass of each marker, curve fitting, or peak finding. In step 508, an average shift is determined based on how the markers have moved relative to their position just before treatment starts. This original or starting position may be determined using multiple techniques including but not limited to CBCT or tomosynthesis involving the first and/or second source-detector pair.

Figure 5B:
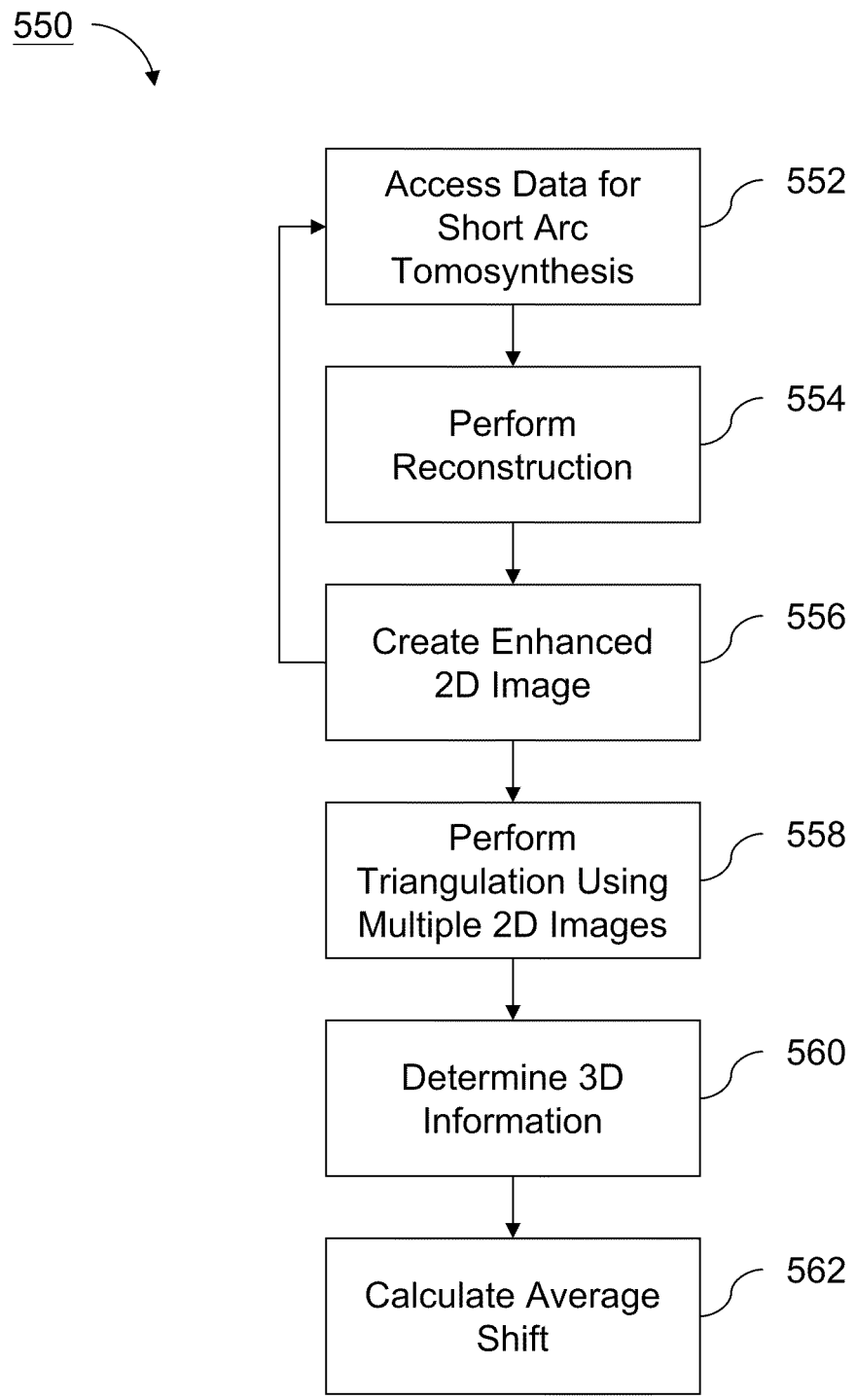
FIG. 5B is a flow chart illustrating a method of processing projection radiographs using short arc tomosynthesis, according to one embodiment of the disclosure.

FIG. 5B is a flow chart illustrating a method 550 processing projection radiographs using short arc tomosynthesis, according to one embodiment of the disclosure. The method 550 can be carried out by the first radiation source 102, the second radiation source 108, or other radiation sources in other implementations. Like FIG. 5A, Step 552 also corresponds to step 202 of FIG. 2 and step 404 of FIG. 4. However, as a variant of the sliding arc tomosynthesis approach described above, the arc length can be smaller for marker tracking using short arc tomosynthesis. As an example, the control system 116 of FIG. 1 here generally accesses 6 projection radiographs for each 3° processing window. The angular range of a processing window for short arc tomosynthesis can be approximately 3 degrees or may correspond to a compromised larger arc length to include approximately minimum 6 projection radiographs. Steps 554, 556, 558, 560 and 562 further illustrate step 204 of FIG. 2 and step 406 of FIG. 4. Similar to FIG. 5A, the reconstruction performed in step 554 also may include techniques such as, without limitation, backprojection or filtering, and the preprocessing techniques possibly utilized in step 554 include techniques such as, without limitation, performing logarithmic transforms.

In step 554, in one implementation, when short arc tomosynthesis reconstructs small volumes, a number of slices are generated by back projecting the input projection radiographs without putting them through 2D spatial filtering. The depth covered by these slices cover several times the depth of the volume of interest. In such an implementation, a 3D filter can be applied to the generated slices to remove the blurred out-of-slice structures for the slices of interest. This method is described in the United States Patent Application No. US 2007/0237290 A1 of Varian Medical Systems, Inc.

In step 556, the control system 116 creates an enhanced 2D image. Unlike the sliding arc tomosynthesis approach of FIG. 5A, which generates 3D information, this short arc tomosynthesis approach combines projection radiographs acquired over a small arc of gantry rotation to generate a 2D image with significant enhancement of the target region. This 2D image is used instead of the original projection radiographs for marker tracking. Steps 552, 554, and 556 are repeated at least once, using a different short arc window, in order to generate multiple 2D images. In one implementation, this short arc can "slide" as in sliding arc tomosynthesis, and the imaging data corresponding to the short arc may be acquired continuously. In another implementation, the imaging data corresponding to the short arc may be acquired with gaps in a certain angular range. In yet another implementation, the imaging data corresponding to the short arc may be acquired at predetermined gantry angles. In still another implementation, the control system 116 of FIG. 1 may determine when to access the imaging data corresponding to the short arc based on optimization considerations.

Figure 6:
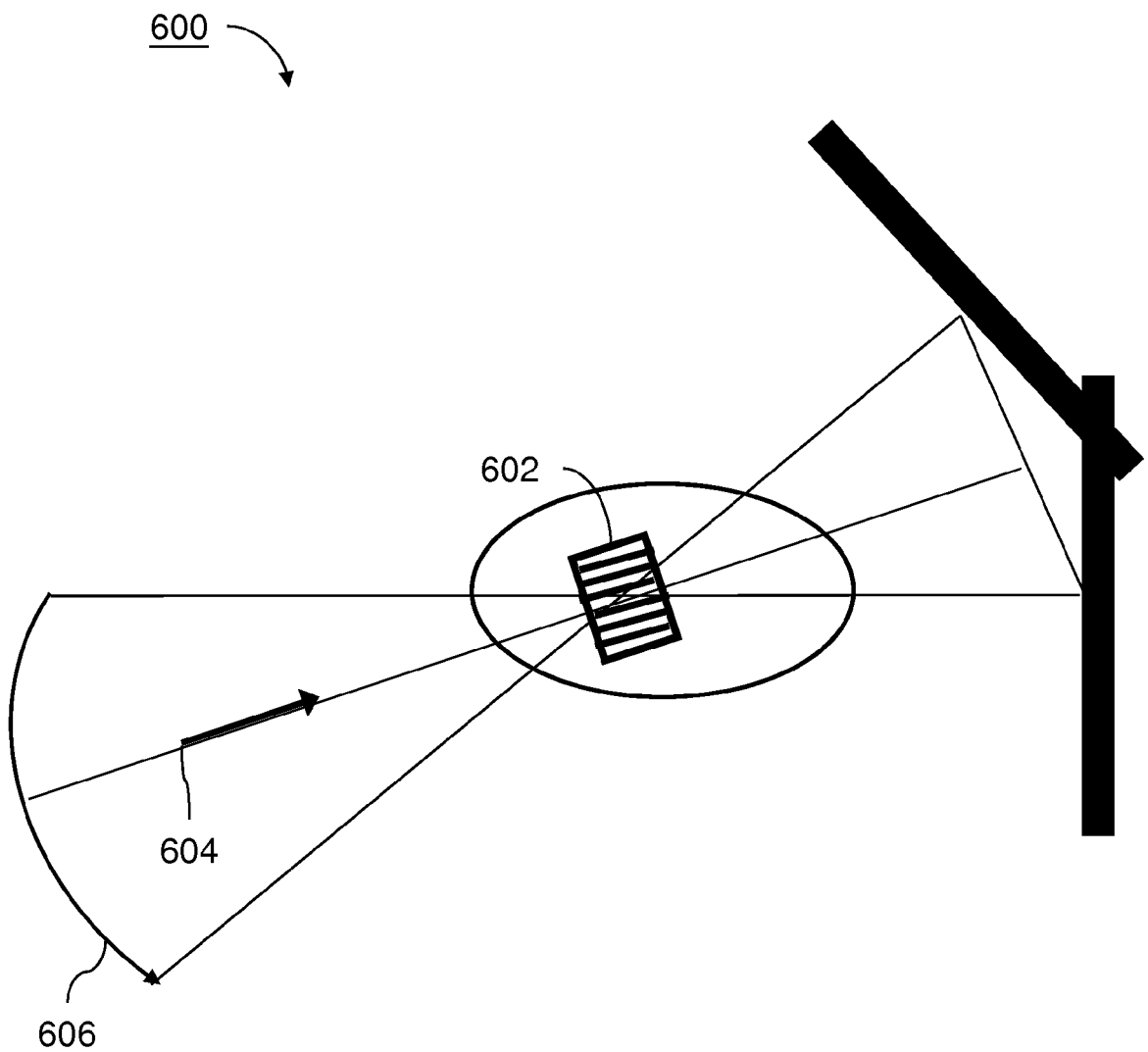
FIG. 6 is a schematic diagram illustrating an axial view of the voxel row, according to one embodiment of the disclosure.

Before describing step 558 of FIG. 5, FIG. 6 is a schematic diagram 600 illustrating an axial view of a voxel row, according to one embodiment of the disclosure. For the purpose of 3D tracking, short arc DTS voxels 602 can be visualized in the planes that are parallel to the imager rotation axis (also referred to as "slice planes" or "lateral planes") and normal to the imaging axis at a center projection 604 of an acquisition arc 606. The voxel dimensions are small in the slice plane and long in the direction parallel to the imaging axis at the arc center (i.e. the radial direction). The long voxel dimension, or large "voxel depth," corresponds to low depth resolution, and is due to the short arc used for tomosynthesis. Depth resolution is determined by triangulation, and is not an objective of individual images. Short arc tomosynthesis enhances the image of markers in the presence of noise and reduces the effect of overlaying objects outside the volume occupied by the markers. For example, in the case of multiple markers in prostate, the voxel depth can be about 2 to 3 cm, thus minimizing the effect of any overlaying bony structures or external objects. This voxel depth is achievable with short arcs of 2 to 3 degrees.

Referring back to FIG. 5, in step 558, the control system 116 performs triangulation using multiple 2D images generated from step 556. Three dimensional tracking by triangulation uses two or more images that are reconstructed from short arcs centered at different gantry angles. Geometrically, the 2D images of the markers can be viewed as projection radiographs of the markers onto a new image plane that is defined by the slice plane 602. In one implementation, triangulation using two of these images can be achieved by intersecting the two lines that go through the 2D position of the target, found in each image, and where each line also connects to the radiation source position for the corresponding arc center. This intersection of the two lines is also referred to as a triangulated position. In such an implementation, the geometric calibration parameters of each 2D image can vary with the gantry angle corresponding to the short arc center; the source-to-image plane distance is the normal distance of the radiation source position corresponding to arc center, to the slice plane; this is different from source-to-flat panel (physical image sensor) distance and can vary with the gantry angle corresponding to short arc center. Similar to FIG. 5A, 3D information is determined in step 560, and the average shift is calculated in step 562.

Figure 7:
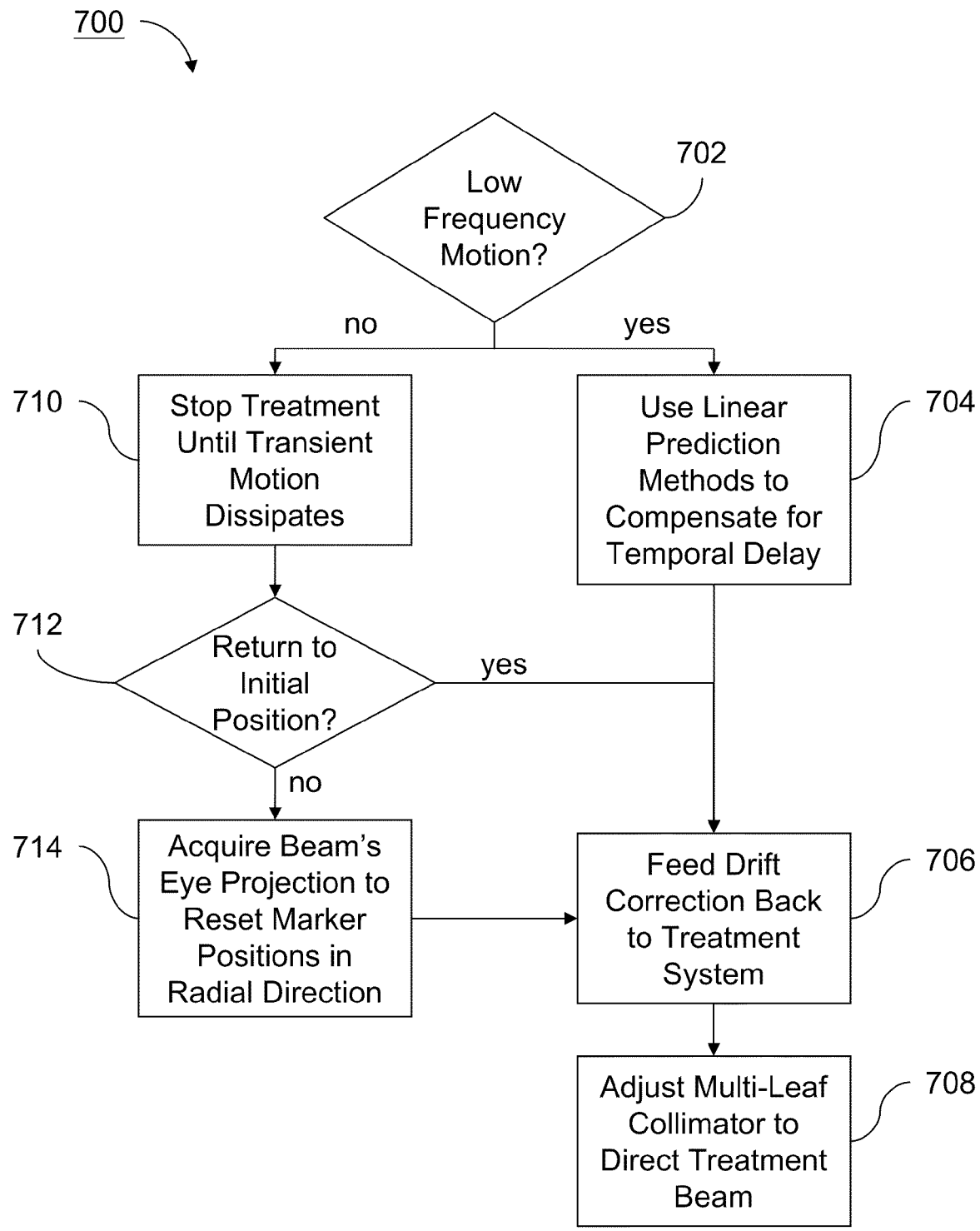
FIG. 7 is a flow chart illustrating a method of adjusting treatment real-time, according to one embodiment of the disclosure.

FIG. 7 is a flow chart illustrating a method 700 of performing real-time treatment adjustment, according to one embodiment of the disclosure. In one implementation, after the control system 116 of FIG. 1 calculates an average shift as shown in FIG. 5A and FIG. 5B and discussed above, drift data for tracking or repositioning based on the average shifts from two processing windows are also calculated. Specifically, in one implementation, the control system 116 determines whether low frequency motion has occurred in step 702. If low frequency motion is indeed detected, the control system 116 is configured to use linear prediction methods to compensate for the temporal delay in step 704. The average temporal delay in seconds ($T_r$) in the radial direction is given by the equation $T_r = N\Delta t/2$, where N is the number of projection radiographs processed, and $\Delta t$ is the sampling period of the projection radiographs. In step 706, the drift data is fed back to the treatment system. In step 708, the multi-leaf collimator will be adjusted so that the first radiation source 102 is directed to compensate for the drift.

If in step 702 the control system 116 instead determines that a transient motion has occurred, then in step 710 treatment is stopped until the transient motion dissipates. In step 712, the control system 116 determines whether the transient motion has returned to the initial position. If so, the drift data is fed back to the treatment system and the multi-leaf collimator will be adjusted, in steps 706 and 708, respectively. If not, in step 714, the control system 116 can acquire a beam's eye projection from the first radiation source 102 to reset marker positions in the radial direction. After the marker positions are reset, the drift data is again fed back to the treatment system in step 706 and the multi-leaf collimator is adjusted to compensate the drift data in step 708.

In other embodiments, in conjunction with FIG. 1, the control system 116 is configured to not only adjust treatment beams from the first radiation source 102, but also interleave imaging beams from the second radiation source 108, imaging beams from the first radiation source 102, treatment beams from the first radiation source 102, and other data signals.

In the illustrated embodiment, the methods 400, 500, and 550 can be performed while treatment occurs. In an alternative implementation, the methods 400, 500, and 550 can be performed using the projection radiographs acquired prior to a current treatment session. In some implementations, in conjunction with FIG. 1, the 3D information of the markers determined using the methods 500 and 550 can also be used to verify a location of a target region, to track a movement of the target region, and/or to control an operation of the first radiation source 102, and/or the collimator. In the illustrated embodiment, the method 700 adjusts the multi-leaf collimator in real-time during treatment. In other implementations, the method 700 can adjust gantry speed, delivery dose, or other treatment parameters.

One embodiment of the disclosure may be implemented as a program product for use with a computing device. The programming instructions of the program product define functions of the embodiments (including the methods described herein) and can be contained on a variety of computer-readable storage media. Illustrative computer-readable storage media include, but are not limited to: (i) non-writable storage media (e.g., read-only memory devices within a computer such as CD-ROM disks readable by a CD-ROM drive, DVD disks readable by a DVD driver, ROM chips or any type of solid-state non-volatile semiconductor memory) on which information is permanently stored; and (ii) writable storage media (e.g., floppy disks within a diskette drive, hard-disk drive, CD-RW, DVD-RW, solid-state drive, flash memory, or any type of random-access memory) on which alterable information is stored. Such computer-readable storage media, when carrying computer-readable instructions that direct the functions of the present disclosure, are embodiments of the present disclosure.

While the foregoing is directed to embodiments of the disclosure, other and further embodiments of the disclosure may be devised without departing from the basic scope thereof. Therefore, the above examples, embodiments, and drawings should not be deemed to be the only embodiments, and are presented to illustrate the flexibility and advantages of the disclosure as defined by the following claims.

We claim:

1. A method of determining a movement of a target region using tomosynthesis, comprising:
    accessing a first set of projection radiographs of the target region over a first processing window defined by a first range of projection angles;
    accessing a second set of projection radiographs of the target region over a second processing window defined by a second range of projection angles, wherein some of the first range of projection angles in the first processing window overlap with the second range of projection angles in the second processing window; and
    comparing a first positional information derived from the first set of the projection radiographs and a second positional information derived from the second set of the projection radiographs to determine the movement of the target region.

2. The method of claim 1, wherein the first set of projection radiographs and the second set of projection radiographs are acquired by rotating a first radiation source and a first flat panel detector about the target region in an arcuate manner.

3. The method of claim 1, wherein the first set of projection radiographs and the second set of projection radiographs are acquired by moving a first radiation source that aims at the target region in a first direction and moving a first flat panel detector in a second direction.

4. The method of claim 3, further comprising moving the first radiation source and the first flat panel detector along sides of the target region.

5. The method of claim 1, wherein the first set of projection radiographs and the second set of projection radiographs are acquired by rotating a first radiation source that aims at the target region in a first plane, wherein the first plane is in parallel to a second plane that a first flat panel detector is in.

6. The method of claim 1, wherein the first set of projection radiographs and the second set of projection radiographs are acquired by rotating a first radiation source that aims at the target region in a first plane and rotating a first flat panel detector in a second plane.

7. A treatment system configured to determine a movement of a target region using tomosynthesis, comprising:
    a rotatable gantry;
    a first radiation source;
    a first flat panel detector; and
    a control system, wherein the control system is configured to
    access a first set of projection radiographs of the target region over a first processing window defined by a first range of projection angles;
    access a second set of projection radiographs of the target region over a second processing window defined by a second range of projection angles, wherein some of the first range of projection angles in the first processing window overlap with the second range of projection angles in the second processing window; and
    compare a first positional information derived from the first set of the projection radiographs and a second positional information derived from the second set of the projection radiographs with the first positional information to determine the movement of the target region.

8. The treatment system of claim 7, wherein the control system is further configured to rotate the first radiation source and also the first flat panel detector about the target region in an arcuate manner to acquire the first set of projection radiographs and the second set of the projection radiographs.

9. The treatment system of claim 7, wherein the control system is further configured to move the first radiation source that aims at the target region in a first direction and move the first flat panel detector in a second direction to acquire the first set of projection radiographs and the second set of the projection radiographs.

10. The treatment system of claim 9, wherein the control system is further configured to move the first radiation source and the first flat panel detector along sides of the target region.

11. The treatment system of claim 7, wherein the control system is further configured to move the first radiation source independently from rotation of the rotatable gantry to acquire the first set of projection radiographs and the second set of the projection radiographs.

12. The treatment system of claim 7, wherein the control system is further configured to rotate the first radiation source that aims at the target region in a first plane, which is in parallel to a second plane that the first flat panel detector is in, to acquire the first set of projection radiographs and the second set of the projection radiographs.

13. The treatment system of claim 7, wherein the control system is further configured to rotate the first radiation source that aims at the target region in a first plane and rotate the first flat panel detector in a second plane to acquire the first set of projection radiographs and the second set of the projection radiographs.

14. A computer readable medium containing a sequence of programming instructions for determining a movement of a target region using tomosynthesis, which when executed by a processor in a treatment system, causes the treatment system to:
    access a first set of projection radiographs of the target region over a first processing window defined by a first range of projection angles;
    access a second set of projection radiographs of the target region over a second processing window defined by a second range of projection angles, wherein some of the first range of projection angles in the first processing window overlap with the second range of projection angles in the second processing window; and
    compare a first positional information derived from the first set of the projection radiographs and a second positional information derived from the second set of the projection radiographs with the first positional information to determine the movement of the target region.

15. The computer readable medium of claim 14, further comprising a sequence of programming instructions, which when executed by the processor, causes the treatment system to rotate a first radiation source and a first flat panel detector about the target region in an arcuate manner to acquire the first set of projection radiographs and the second set of the projection radiographs.

16. The computer readable medium of claim 14, further comprising a sequence of programming instructions, which when executed by the processor, causes the treatment system to to move the first radiation source that aims at the target region in a first direction and move the first flat panel detector in a second direction to acquire the first set of projection radiographs and the second set of the projection radiographs.

17. The computer readable medium of claim 16, further comprising a sequence of programming instructions, which when executed by the processor, causes the treatment system to move the first radiation source and the first flat panel detector along sides of the target region.

18. The computer readable medium of claim 14, further comprising a sequence of programming instructions, which when executed by the processor, causes the treatment system to rotate the first radiation source that aims at the target region in a first plane, which is in parallel to a second plane that the first flat panel detector is in, to acquire the first set of projection radiographs and the second set of the projection radiographs.

19. The computer readable medium of claim 14, further comprising a sequence of programming instructions, which when executed by the processor, causes the treatment system to rotate the first radiation source that aims at the target region in a first plane and rotate the first flat panel detector in a second plane to acquire the first set of projection radiographs and the second set of the projection radiographs.

* * * * *